(12) United States Patent
Zentgraf et al.

(10) Patent No.: US 9,297,812 B2
(45) Date of Patent: Mar. 29, 2016

(54) MEANS AND METHODS FOR DIAGNOSING CANCER USING AN ANTIBODY WHICH SPECIFICALLY BINDS TO BRAF V600E

(75) Inventors: Hanswalter Zentgraf, Heidelberg (DE); Ulrike Zentgraf, legal representative, Heidelberg (DE); Andreas Von Deimling, Schriesheim (DE); David Capper, Mannheim (DE)

(73) Assignees: Deutsches Krebsforschungzentrum, Heidelberg (DE); Ruprecht-Karl-Universität Heidelberg, Heidelberg (DE)

( * ) Notice: Subject to any disclaimer, the term of this patent is extended or adjusted under 35 U.S.C. 154(b) by 251 days.

(21) Appl. No.: 13/877,035

(22) PCT Filed: Sep. 30, 2011

(86) PCT No.: PCT/EP2011/067092
§ 371 (c)(1),
(2), (4) Date: Jun. 24, 2013

(87) PCT Pub. No.: WO2012/042009
PCT Pub. Date: Apr. 5, 2012

(65) Prior Publication Data
US 2013/0266962 A1    Oct. 10, 2013

Related U.S. Application Data

(60) Provisional application No. 61/388,158, filed on Sep. 30, 2010, provisional application No. 61/503,950, filed on Jul. 1, 2011.

(51) Int. Cl.
| | |
|---|---|
| *A61K 38/00* | (2006.01) |
| *G01N 33/68* | (2006.01) |
| *C07K 16/30* | (2006.01) |
| *G01N 33/543* | (2006.01) |
| *G01N 33/574* | (2006.01) |
| *G01N 33/50* | (2006.01) |

(52) U.S. Cl.
CPC ............ *G01N 33/6893* (2013.01); *C07K 16/30* (2013.01); *G01N 33/5088* (2013.01); *G01N 33/543* (2013.01); *G01N 33/5743* (2013.01); *G01N 33/57426* (2013.01)

(58) Field of Classification Search
None
See application file for complete search history.

(56) References Cited

U.S. PATENT DOCUMENTS 6,735,531 B2 * 5/2004 Rhett et al. .............. 702/31
2010/0203109 A1   8/2010 Herlyn et al.

FOREIGN PATENT DOCUMENTS

| EP | 2 036 990 B1 | 2/2014 |
|---|---|---|
| JP | 2009-077712 A | 4/2009 |
| WO | WO 2005/047542 A1 | 5/2005 |
| WO | WO 2007/002811 A2 | 1/2007 |
| WO | WO 2009/036188 A2 | 3/2009 |

OTHER PUBLICATIONS

Basolo et al., "Correlation between the BRAF V600E mutation and tumor invasiveness in papillary thyroid carcinomas smaller than 20 millimeters: analysis of 1060 cases," *J. Clin. Endocrinol. Metab.* 95:4197-4205, 2010.
Capper et al., "Assessment of BRAF V600E mutation status by immunohistochemistry with a mutation-specific monoclonal antibody," *Acta Neuropathol*, 122(1):11-19, 2011.
Chapman et al., "Early efficacy signal demonstrated in advanced melanoma in a phase I trial of the oncogenic BRAF-selective inhibitor PLX4032," *European Journal of Cancer Supplement*, Abstract # 6BA, 7:5, 2009.
Davies et al., "Mutations of the BRAF gene in human cancer," *Nature*, 417(27):949-954, 2002 (w/Suppl material; 16 pages).
French et al., "Prognostic Significance of Defective Mismatch Repair and BRAF V600E in Patients with Colon Cancer," *Clin Cancer Res*, 14(11):3408-3415, 2008.
Galfrè et al., "Preparation of Monoclonal Antibodies: Strategies and Procedures," *Meth. Enzymol.*, 73:3-46, 1981.
Köhler et al., "Continuous cultures of fused cells secreting antibody of predefined specificity," *Nature*, 256:495-497, 1975.
Pardi et al., "Aryl Hydrocarbon Receptor-Interacting protein (AIP) mutations occur rarely in sporadic parathyroid adenomas," *J Clin Endocrinol Metab* (published ahead of print Apr. 30, 2013 as doi:10.1210/jc.2012-4029).
Poulikos et al., "RAF inhibitors transactivate RAF dimers and ERK signalling in cells with wild-type BRAF," *Nature*, 464:427-31, 2010.
Sithanandam et al., "Complete coding sequence of a human B-raf cDNA and detection of B-raf protein kinase with isozyme specific antibodies," *Oncogene*, 5(12):1775-80, 1990.
Tiacci et al., "BRAF Mutations in Hairy-Cell Leukemia," *New England Journal of Medicine*, 364(24):2305-2315, 2011.
Decision to Grant a Patent issued in JP 2013-530750 on Jan. 26, 2016 (3 pages) in Japanese.

* cited by examiner

*Primary Examiner* — Sean Aeder
*Assistant Examiner* — Julie Wu
(74) *Attorney, Agent, or Firm* — Klarquist Sparkman, LLP

(57) ABSTRACT

The present invention relates to the field of diagnostic tests and diagnostic tools. Specifically, contemplated is to a method for diagnosing cancer in a sample of a subject suspected to suffer from cancer comprising contacting the sample with an antibody which specifically binds to the epitope characterized by SEQ ID NO 1 on a BRAF polypeptide under conditions which allow for binding of said antibody to the epitope and determining binding of the antibody to the epitope, whereby cancer is diagnosed. Further contemplated are antibodies which specifically bind to the epitope characterized by SEQ ID NO 1 on a BRAF polypeptide and a device or kit comprising such antibodies.

11 Claims, 4 Drawing Sheets

Clone 263

MEANS AND METHODS FOR DIAGNOSING CANCER USING AN ANTIBODY WHICH SPECIFICALLY BINDS TO BRAF V600E

CROSS REFERENCE TO RELATED APPLICATIONS

This is the U.S. National Stage of International Application No. PCT/EP2011/067092, filed Sep. 30, 2011, which was published in English under PCT Article 21(2), which in turn claims the benefit of U.S. Provisional Application No. 61/503,950, filed Jul. 1, 2011 and U.S. Provisional Application No. 61/388,158, filed Sep. 30, 2010. The provisional applications are incorporated herein in their entirety.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. The Sequence Listing is submitted as an ASCII text file, created on Mar. 28, 2013, ~4 KB, which is incorporated by reference herein.

The present invention relates to the field of diagnostic tests and diagnostic tools. Specifically, contemplated is to a method for diagnosing cancer in a sample of a subject suspected to suffer from cancer comprising contacting the sample with an antibody which specifically binds to the epitope characterized by SEQ ID NO 1 on a BRAF polypeptide under conditions which allow for binding of said antibody to the epitope and determining binding of the antibody to the epitope, whereby cancer is diagnosed. Further contemplated are antibodies which specifically bind to the epitope characterized by SEQ ID NO 1 on a BRAF polypeptide and a device or kit comprising such antibodies.

BACKGROUND

Cancer is the second leading cause of death in the United States after cardiovascular disease. One in three Americans will develop cancer in his or her lifetime, and one of every four Americans will die of cancer. Despite profound experience with the traditional therapeutic approaches—resection, radiation and chemotherapy, most of the malignant human tumors still follow a fatal clinical course. A novel development in tumor therapy is so called targeted therapy. This approach relies on the treatment of tumor initiating or promoting molecular alterations which are characteristic for the individual patient's tumor. Knowledge of such alterations might be decisive for the selection of the preferable kind of life prolonging or even curative therapy.

Mutations in the V-RAF MURINE SARCOMA VIRAL ONCOGENE HOMOLOG B1 (BRAF) have been described in multiple tumor series including melanoma (Davies et al. 2002 Nature 417: 949-54), papillary thyroid carcinoma (Basolo et al. 2010 J Clin Endocrinol Metab 95(9):4197-4205), colon cancer (French et al. 2008 Clin Cancer Res 14: 3408-15), ovarian cancer (Davies et al. 2002 Nature 417: 949-54), and other entities. BRAF is part of the RAS/RAF/MEK/ERK-signaling pathway which is involved in cell proliferation. Activation of this pathway results in promotion of malignant transformation.

One of the molecular targets of the targeted therapy approach for cancer therapy is an exchange of amino acid valin by amino acid glutamic acid in codon 600 of the human BRAF gene (V600E). Approximately 8% of all human tumors carry this particular mutation. The V600E mutation in BRAF renders the protein constitutively active. It is especially frequent in melanoma and thyroid tumors. Preclinical analyses indicated selective activity of RAF inhibitors in tumors with BRAF V600E mutation without affecting ERK signaling in normal cells (Poulikakos 2010, Nature 464: 427-30). Therapies targeting this V600E mutation with specific inhibitors are currently in clinical testing (Chapman 2009, European Journal of Cancer Supplements 7: 5).

The gold standard for diagnostic analysis of a BRAF V600E mutation is currently DNA sequencing. However, this method has some limitations: The percentage of tumor cells in the tissue taken for DNA extraction needs to be rather high. Too much contaminant with non tumorous cells will result in a false negative sequencing result. The procedure of DNA analysis is time consuming because at first, suitable material for DNA extraction must be outlined by a pathologist, DNA extraction needs to be performed and then, DNA can be sequenced. The present invention allows identification of even small tumor islets with the BRAF mutations within large areas of normal tissue without the mutation. The analysis of BRAF V600E mutation with the present invention can be performed within a few hours using the equipment available in routine pathology laboratories.

SUMMARY OF THE INVENTION

Therefore, the present invention relates to a method for diagnosing cancer in a sample of a subject suspected to suffer from cancer comprising:
a) contacting the sample with an antibody which specifically binds to the epitope characterized by SEQ ID NO 1 on a BRAF polypeptide under conditions which allow for binding of said antibody to the epitope; and
b) determining binding of the antibody to the epitope, whereby cancer is diagnosed.

In a preferred embodiment of the method of the present invention, said antibody is a monoclonal antibody.

In another preferred embodiment of the method of the present invention, said antibody is the antibody produced by the hybridoma clone as deposited under accession number DSM ACC3091.

In a preferred embodiment of the method of the present invention, said diagnosing cancer comprises determining the presence or absence of cancer cells.

In a preferred embodiment of the aforementioned method of the present invention, said cancer cells is within a tissue sample.

In a preferred embodiment of the method of the aforementioned present invention, said tissue sample is a tissue section sample.

In a preferred embodiment of the method of the present invention, said method further comprises the step of recommending an anti-cancer therapy based on the diagnosis obtained in step b).

In a preferred embodiment of the aforementioned method of the present invention, said anti-cancer therapy is selected from the group consisting of: anti-BRAF antisense RNA, siRNA or micro RNA drugs, anti-BRAF antibodies, sorafenib, cetuximab, RAF-265, PLX-4032 and GDC-0879.

The invention relates also to an antibody which specifically binds to the epitope characterized by SEQ ID NO: 1 in the BRAF polypeptide.

In a preferred embodiment of the antibody of the present invention, said antibody is a monoclonal antibody.

The invention further relates to the antibody produced by the hybridoma clone deposited under accession number DSM ACC 3091 with the "DSMZ-Deutsche Sammlung von Mikroorganismen and Zellkulturen GmbH", 38124 Braunschweig, GERMANY on Sep. 8, 2010 according to the Budapest Treaty by "Deutsches Krebsforschungszentrum", Heidelberg, GERMANY.

The invention pertain to a device for diagnosing cancer comprising
a) an analyzing unit comprising an antibody of the invention, wherein said analyzing unit allows for the determination of specific binding of the antibody to the epitope characterized by SEQ ID NO: 1 in the BRAF polypeptide in a sample applied to the analyzing unit; and
b) an evaluation unit which comprises implemented rules for evaluating the binding determined by the analyzing unit and for establishing a diagnosis.

In a preferred embodiment of the device of the present invention, said sample is a tissue sample.

In a preferred embodiment of the aforementioned device of the present invention, said tissue sample is a tissue section sample.

The present invention also relates to a kit for diagnosing cancer comprising an antibody of the present invention.

FIGURES

FIG. 1 shows a Western Blot analysis of different monoclonal antibodies obtained from immunization with the KLH linked immunogenic peptide having SEQ ID NO: 1 as described in the accompanying Examples. Most of the generated hybridoma clones showed also unspecific binding in addition to binding to a 95 kDa putative V600E BRAF band as exemplified by clones 53, 62, and 449. Clone 263 showed specific binding for the 95 kDa V600E BRAF band. The antibody produced by this hybridoma clone was further tested in tissue sections. The hybridoma clone itself was deposited under accession number DSM ACC 3091 with the "DSMZ—Deutsche Sammlung von Mikroorganismen and Zellkulturen GmbH", 38124 Braunschweig, GERMANY on Sep. 8, 2010 according to the Budapest Treaty by "Deutsches Krebsforschungszentrum", Heidelberg, GERMANY.

Figure 4:
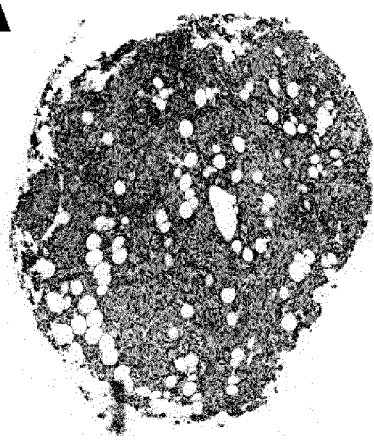
Figure 4:
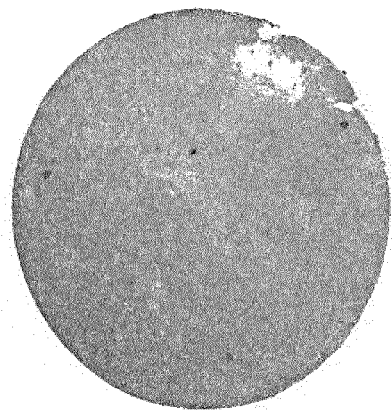
Figure 4:
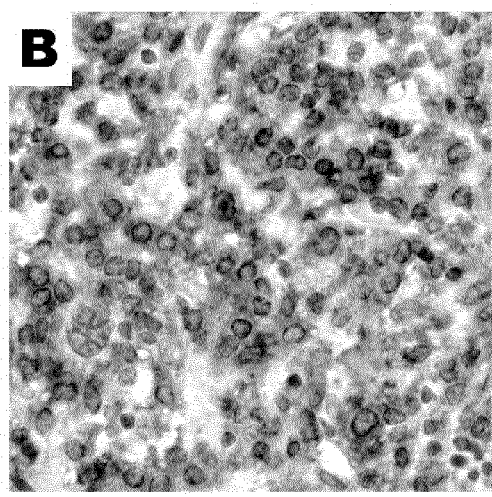
Figure 4:
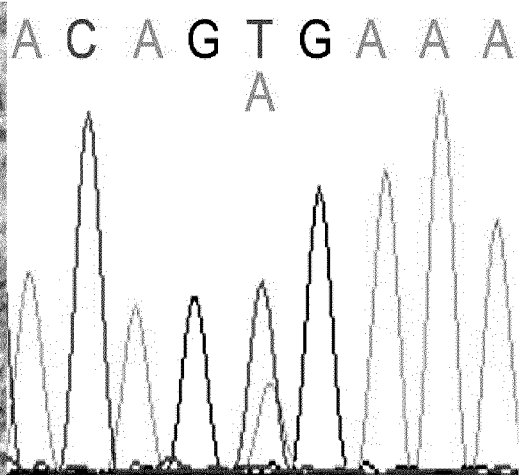
Figure 4:
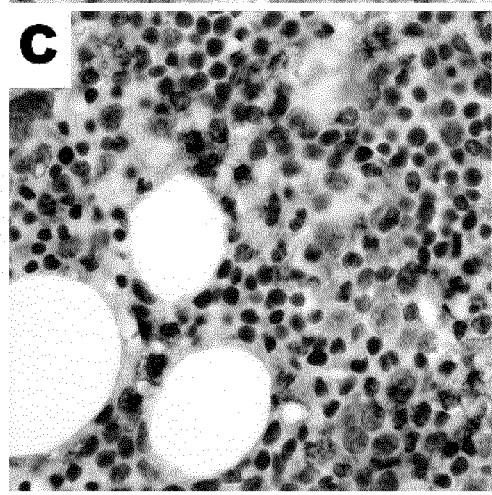
Figure 4:
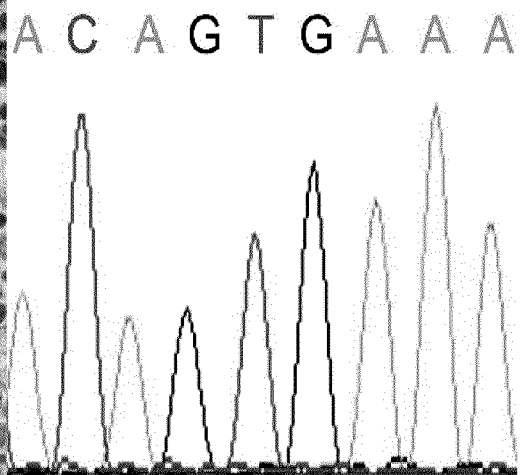

FIG. 4 shows BRAF-V600E detection by immunohistochemistry and direct sequencing; Representative TMA cores (A) of HCL (left) and splenic marginal zone lymphoma (right) stained with VE1. Representative sections of bone marrow biopsies (400× original magnification) with different tumor burden (in case B—100%, case C—10%) immunostained with VE1 (left column) and corresponding DNA sequences containing the BRAF codon 600. Minimal infiltration is detectable by VE1 immunohistochemistry in case C whereas DNA sequencing does not detect the mutation. Microscopic figures were taken with Olympus BX-51 light microscope equipped with DP50-CCD camera and processed with Cell-A Software (all from Olympus, Hamburg, Germany)

DETAILED DESCRIPTION OF THE INVENTION

The present invention relates to a method for diagnosing cancer in a sample of a subject suspected to suffer from cancer comprising:
a) contacting the sample with an antibody which specifically binds to the epitope characterized by SEQ ID NO 1 on a B-Raf polypeptide under conditions which allow for binding of said antibody to the epitope; and
b) determining binding of the antibody to the epitope, whereby cancer is diagnosed.

The term "diagnosing" as used herein means assessing whether a subject suffers from cancer, or not. As will be understood by those skilled in the art, such an assessment is usually not intended to be correct for all (i.e. 100%) of the subjects to be identified. The term, however, requires that a statistically significant portion of subjects can be identified (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

More preferably, at least 60%, at least 70%, at least 80% or at least 90% of the subjects of a population can be properly identified by the method of the present invention. Diagnosing according to the present invention includes applications of the method in monitoring, confirmation, and sub-classification of the relevant cancer.

Moreover, diagnosing also includes establishing a prognosis for a subject. A subject which is diagnosed to suffer from cancer according to the method of the present invention shall have cancer cells expressing the BRAF V600E polypeptide. The presence of the BRAF V600E is a predictive indicator for a possibly poor outcome in the subjects. Thus, the method of the present invention can also be applied for risk stratification approaches and, thus, for determining the amount of intensive care and hospitalization which will be required for an individual subject suffering from cancer.

The term "cancer" as used herein refers to any malignant neoplasm. The malignant neoplasm refers to diseases resulting from the undesired growth, the invasion, and under certain conditions metastasis of impaired cells in an organism. The cells giving rise to cancer are genetically impaired and have usually lost their ability to control cell division, cell migration behavior, differentiation status and/or cell death machinery. Most cancers form a tumor but some hematopoietic cancers, such as leukemia, do not. The cancer in accordance with the present invention shall comprise cancer cells expressing a BRAF V600E mutant polypeptide as specified elsewhere herein. Preferred types of cancer are selected from the group consisting of: melanomas, papillary thyroid carcinomas, colon carcinomas, ovarian cancer and breast cancer. Most preferably, the cancer is a melanoma or a papillary thyroid carcinoma due to the very high percentage of BRAF V600E mutations of 50% or higher in these cancer entities. Also preferably, the cancer according to the invention is a hematopoietic cancer, preferably leukemia including neoplasia of mature B-cells. More preferably, said cancer is hairy cell leukemia. Symptoms and staging systems for the different cancers are well known in the art and described in standard text books of pathology. Cancer as used herein encompasses any stage, grade, morphological feature, invasiveness, aggressiveness or malignancy of the cancer or the tissue or organ affected thereby.

The term "sample" refers to a sample of separated cells or to a sample from a tissue or an organ. Tissue or organ samples may be obtained from any tissue or organ by, e.g., biopsy. Separated cells may be obtained from the body fluids, such as lymph, blood, plasma, serum, liquor and the like, or from the tissues or organs by separating techniques such as centrifugation or cell sorting. Preferably, cell-, tissue- or organ samples are obtained from those cells, tissues or organs which express or produce the peptides referred to herein. The sample can be obtained from the subject by routine techniques which are well known to the person skilled in the art, e.g., open biopsy including aspiration of tissue or cellular material from a subject. For those areas which cannot be easily reached via an open biopsy, a surgery and, preferably, minimal invasive surgery can be performed.

The term "subject" as used herein relates to animals, preferably mammals, and, more preferably, humans. Preferably, the method of the present invention will be applied for subjects suspected to either suffer from cancer in light of clinically apparent symptoms or subjects suspected to suffer from cancer due to a potential increased predisposition The term "antibody" refers to all types of antibodies which specifically bind to the BRAF V600E polypeptide. An antibody of the invention shall specifically bind to the epitope characterized by the amino acid sequence shown in SEQ ID NO: 1. Preferably, the antibody of the present invention is a monoclonal antibody, a polyclonal antibody, a single chain antibody, a chimeric antibody or any fragment or derivative of such antibodies being still capable of binding the BRAF V600E polypeptide and, in particular the epitope shown in SEQ ID NO: 1 specifically. Such fragments and derivatives comprised by the term antibody as used herein encompass a bispecific antibody, a synthetic antibody, an Fab, F(ab)2 Fv or scFv fragment, or a chemically modified derivative of any of these antibodies. Chemical modifications envisaged preferably by the present invention include those which aim to couple the antibody to a detectable marker as specified elsewhere in this specification. Specific binding as used in the context of the antibody of the present invention means that the antibody does not cross react with other polypeptides including the wildtype BRAF or BRAF muteins other than the BRAF V600E muant polypeptide or, even more preferably, does not cross react with any epitope other than the epitope shown in SEQ ID NO: 1. Specific binding can be tested by various well known techniques. Preferably, specific binding can be tested as described in the accompanying Examples. Antibodies or fragments thereof, in general, can be obtained by using methods which are described, e.g., in Harlow and Lane "Antibodies, A Laboratory Manual", CSH Press, Cold Spring Harbor, 1988.

Monoclonal antibodies can be prepared by the techniques which comprise the fusion of mouse myeloma cells to spleen cells derived from immunized mammals and, preferably, immunized mice (Köhler 1975, Nature 256, 495, and Galfré1981, Meth. Enzymol. 73, 3). Preferably, an immunogenic peptide having the epitope shown in SEQ ID NO: 1 is applied to a mammal. A peptide having the sequence shown in SEQ ID NO: 1 is preferably conjugated to a carrier protein, such as bovine serum albumin, thyroglobulin, and keyhole limpet hemocyanin (KLH). Depending on the host species, various adjuvants can be used to increase the immunological response. Such adjuvants encompass, preferably, Freund's adjuvant, mineral gels, e.g., aluminum hydroxide, and surface active substances, e.g., lysolecithin, pluronic polyols, polyanions, peptides, oil emulsions, keyhole limpet hemocyanin, and dinitrophenol. Monoclonal antibodies which specifically bind to the epitope having SEQ ID NO: 1 in BRAF V600E can be subsequently prepared using the well known hybridoma technique, the human B cell hybridoma technique, and the EBV hybridoma technique. Preferably, the antibody of the invention can be obtained by the method described in the accompanying Examples below. Preferably, the antibody is a monoclonal antibody or a derivative thereof as described above. More preferably, the antibody is the antibody produced by the hybridoma clone as deposited under accession number DSM ACC3091 with the "DSMZ-Deutsche Sammlung von Mikroorganismen and Zellkulturen GmbH", 38124 Braunschweig, GERMANY on Sep. 8, 2010 according to the Budapest Treaty by "Deutsches Krebsforschungszentrum", Heidelberg, GERMANY.

The term "BRAF polypeptide" as used herein refers to the polypeptide encoded by the v-Raf murine sarcoma viral oncogene homolog B1 oncogen. The BRAF polypeptide is a serine/threonine kinase which acts in the RAS/RAF/MEK/ERK-signaling pathway being involved in cell proliferation. Activation of this pathway results in promotion of malignant transformation. The structure of the BRAF oncogene and the BRAF polypeptide are well known in the art. Preferably, BRAF polypeptide refers to the human BRAF polypeptide as disclosed by Sithanandam 1990, Oncogene 5 (12): 1775-80 and variants of said specific BRAF polypeptide which include allelic variants, orthologs and homolgs. Orthologs of human BRAF in other organisms, e.g., in rodents are also well known in the art. The BRAF polypeptide referred to in accordance with the method of the present invention comprises an epitope as shown in SEQ ID NO: 1 and, thus, has an valine (V) into glutamic acid (E) amino acid exchange at amino acid position 600 or an amino acid position corresponding thereto.

Contacting the sample as referred to herein refers to bringing the antibody and the sample into physical contact thereby allowing specific binding of the antibody to the epitope as shown in SEQ ID NO: 1 on the BRAF V600E polypeptide if comprised by the sample. It will be understood that contacting as meant herein is carried out for a time and under conditions sufficient for allowing the antibody to bind specifically to the BRAF V600E polypeptide. Depending on the nature of the sample, pre-treatment steps might be necessary in order to release the BRAF V600E or to de-mask the epitope in the BRAF V600E polypeptide so that the antibody has access and can specifically bind thereto. Moreover, dependent on the kind of sample, the handling might be different. For example, a tissue sample which shall be analyzed for the presence or absence of a BRAF V600E polypeptide is, preferably, homogenized and the proteins comprised by the tissue are isolated and separated, e.g., by SDS PAGE or other protein separation methods. The separated proteins are analyzed for the presence or absence of the BRAF V600E polypeptide by immunological methods such as Western Blot using the antibody defined herein above. These methods also include incubation steps which allow specific binding of the antibody to the BRAF V600E polypeptide. In order to increase the specificity washing steps are to be carried out. How to carry out such measures is well known to the person skilled in the art. If a tissue section is used as a sample (i.e. a tissue section sample), it will be understood that it is envisaged to analyze not only the presence or absence of the BRAF V600E polypeptide but also the cellular or sub cellular localization thereof. Accordingly, the tissue shall be kept intact and may be also stained by histochemical staining techniques prior or after antibody binding. Suitable techniques which allow for immunostaining of tissue sections are well known to the person skilled in the art. Dependent on whether the tissue section sample has been embedded in an embedding medium, such as paraffin, removal of the said embedding medium might be necessary. The relevant techniques are also well known in the art.

Determining binding of the antibody as used herein refers to the detection of the antibody which is specifically bound to the BRAF V600E polypeptide comprised by the sample, if any. Detection methods for antibodies which are specifically bound to an antigen are also well known in the art. Preferably, the antibody to be applied in the method of the present invention itself can be coupled to a detectable marker such as a radioactive isotope (e.g., radioactive isotopes of Iodide Technetium), fluorescent or chemoluminescent agents (e.g., FITC, rhodamin), an enzyme which is capable of generating a detectable signal by converting a substrate (e.g., horseradish peroxidase, firefly luciferase, or beta galactosidase), a fluorescent protein (e.g., green-, blue- or red- fluorescent protein). Suitable detectable markers are well known in the art. Also preferably, the antibody to be applied in the method of the present invention can be coupled to an agent that is capable of attracting a detection agent. Such an agent may be biotin. In such a case an avidin- or streptavidin coupled detection agent can be used which upon binding of the biotin of the bound antibody will serve as a detectable marker. Suitable detectable markers in such a case are those referred to above, more preferably, an enzyme shall be used as a detectable marker in such a case. Furthermore, a secondary antibody may be used for detection of the first antibody, i.e. the antibody to be applied in the method of the present invention which is bound to the BRAF V600E polypeptide of the sample. Such a secondary antibody shall be coupled to a detectable marker as describe above. Thus, in the latter case, the secondary antibody will upon binding to the first antibody generate a detectable signal and thereby enables the detection of the bound first antibody. The principle of detection of bound antibodies with a secondary antibody is well known in the art and routinely applied, e.g., for determining antibody binding on tissue sections. Dependent on the type of detectable marker, different detection methods can be applied using a reader system for the signal generated by the detectable marker. Such systems include automatic signal reader device, such as an ELISA or RIA reader, but also microscopic device for manual or automatic detection of the detectable signal. Moreover, the reader system may determine additional information of the sample, e.g., a microscopic system may display the cells of a tissue section optically or an automated signal reader may determine further biomarkers comprised by the sample in addition.

In general, it was surprisingly found that the antibody described in accordance with the method of the present invention is useful for diagnosing cancer as specified herein on samples from a subject suspect to suffer from the said cancer. The method of the present invention allows for a fast, simple and reliable analysis of the BRAF status in a subject and, thus, for the diagnosis of cancer. Diagnostic results, which are an important basis for the clinician or pathologist for deciding on possible therapies, for prognosis and clinical health care management and/or for classifying the cancer properly, can be generated faster, and the reliability is enhanced because in contrast to gene sequencing analysis also individual tumor cells within otherwise inconspicuous tissue can be detected even in cases where the quality of the sample of the cancer is poor.

In a preferred embodiment of the method of the present invention, said diagnosing cancer comprises determining the presence or absence of cancer cells. Preferably, said cancer cells are within a tissue sample and, more preferably, said tissue sample is a tissue section sample.

Cancer can be preferably diagnosed by determining the presence of cancer cells in a sample. If a cancer cell is identified in a sample, the suspicion that the subject indeed suffers from cancer can be confirmed. Likewise, the absence of cancer cells in a sample is, preferably, indicative for a sample from a subject which shall not suffer from cancer. Preferably, the sample in the latter aspect is a sample which is representative for the cancer in a subject suspected to suffer therefrom. For example, a sample shall be taken from those tissues which appear to be affected by the cancer and which are the basis for suspecting the subject to suffer from the cancer. It will be understood that in such an aspect of the invention, the sample shall not be taken from tissues which are known not to be affected or which are not suspected to be affected from the cancer since such sample may result in false negative diagnostic results.

In particular, where tissue samples and, preferably, tissue section samples are used in the method of the present invention, the diagnosis also encompasses the identification of the individual cancer cells. Accordingly, the method of the present invention can be applied to image cancer cells in a tissue or tissue section in order to determine the extent of the cancer and/or the homogeneity of the cancer. The determination of the extent of a cancer within a tissue affected thereby is crucial for drug based therapies and, in particular, surgery where it needs to be confirmed by tissue biopsy that all parts of the cancer are indeed removed from the affected tissue or organ. In some aspects, there might be cancer cells which are not identified by the method of the present invention but which, e.g., due to their morphology are apparent cancer cells. A cancer which in addition to cancer cells identified by the method of the present invention comprises such cancer cells which cannot be identified by the method of the present invention may be treated by a combination of drugs rather than by one drug alone.

In a preferred embodiment of the method of the present invention, said method further comprises the step of recommending an anti-cancer therapy based on the diagnosis obtained in step b).

The term "recommending" as used herein refers to making a recommendation for an anti-cancer therapy or excluding (i.e. not recommending) a certain anti cancer therapy for a subject. Such a recommendation shall serve optionally together with other information, e.g., information from histopathological investigations, as a basis for a clinician to apply a certain anti-cancer therapy for an individual subject, or not. Based on the diagnosis established in step b) of the method of the present invention, i.e. the diagnosis of "cancer" or "no cancer", a recommendation for an anti-cancer therapy will be made. It will be understood that only in cases where the diagnosis of "cancer" has been established by the method of the present invention, the recommendation for the anti-cancer therapy shall be made. In cases where "no cancer" is established as diagnosis based on the method of the present invention, the recommendation would be to refrain from an anti-cancer therapy. As set forth above, further information from the subject from which the sample originates can be used as well for improving the recommendation. In an aspect, a combined anti-cancer therapy, e.g., with different anti tumor drugs, can be recommended if the method of the present invention identifies cancer cells but if further cancer cells which are not identified by the method of the present invention are detected in the investigated cancer, e.g., by histopathological analyses.

The term "anti-cancer therapy" as used herein encompasses therapies which are surgery-based therapies, radiation-based therapies, drug-based therapies or combinations thereof. The said drug-based anti-cancer therapy is, preferably, a therapy which affects the B-Raf polypeptide and, more preferably, the B-Raf polypeptide having the epitope as shown in SEQ ID NO: 1. Suitable drugs can interfere with the protein activity of the B-Raf polypeptide or with the transcription or translation of the B-Raf oncogene or its transcript. Preferably, said anti-cancer drug is selected from the group consisting of: anti-Raf antisense RNA, siRNA or micro RNA drugs, anti-Raf antibodies, and small molecules. Particular preferred drugs are sorafenib, RAF-265,PLX-4032 or GDC-0879.

Moreover, a recommendation in accordance with the method of the present invention also includes in some cases a negative recommendation for a certain therapy. For example, if the therapeutic target of a drug acts upstream in the signaling cascade of BRAF V600E (which is constitutively active and, thus, independent from an upstream signal activation) it can be reasonably assumed that a drug which aims to inhibit the upstream therapeutic target is not a suitable basis for a sole therapy of a BRAF V600E positive cancer. The EGF receptor (EGFR) has been reported as an upstream activator of BRAF. Moreover, EGFR inhibitors are used in cancer therapy. Of particular interest are the anti-EGFR antibodies such as cetuximab. It is envisaged that in a preferred embodiment of the method of the present invention, recommending also means to exclude a certain therapy for a subject which has been diagnosed to suffer from cancer by the method of the present invention, i.e. a subject which expresses the BRAF V600E polypeptide in the cancer cells. Preferably, such a therapy is a therapy aiming to inhibit the activity of upstream components in the signaling pathway which activates the BRAF polypeptide. More preferably, such a component is EGFR and suitable drugs are anti-EGFR antibodies such as cetuximab.

The present invention also relates to an antibody which specifically binds to the epitope characterized by SEQ ID NO: 1 in the BRAF polypeptide.

More preferably, said antibody is a monoclonal antibody as defined elsewhere herein in more detail.

The present invention furthermore contemplates the antibody produced by the hybridoma clone deposited under accession number DSM ACC 3091 with the "DSMZ-Deutsche Sammlung von Mikroorganismen and Zellkulturen GmbH", 38124 Braunschweig, GERMANY on Sep. 8, 2010 according to the Budapest Treaty by "Deutsches Krebsforschungszentrum", Heidelberg, GERMANY.

An antibody of the invention can be used in immunochemical assays, such as Western blots, ELISAs, radioimmunoassays, immunohistochemical assays, immunoprecipitations, or other immunochemical assays known in the art. In particular, the antibody is useful for carrying of the method of the present invention as described above.

The present invention relates further to a device for diagnosing cancer comprising
a) an analyzing unit comprising an antibody of the present invention as referred to above, wherein said analyzing unit allows for the determination of specific binding of the said antibody to the epitope characterized by SEQ ID NO: 1 in the BRAF polypeptide in a sample applied to the analyzing unit; and
b) an evaluation unit which comprises implemented rules for evaluating the binding determined by the analyzing unit and for establishing a diagnosis.

The term "device" as used herein relates to a system comprising at least the aforementioned analyzing unit and the evaluation unit operatively linked to each other. How to link the units of the device in an operating manner will depend on the type of units included into the device. For example, where units for automatic analysis of a sample are applied, the data obtained by said automatically operating analyzing unit can be processed by, e.g., a computer program in order to obtain the desired results by the evaluation unit. Preferably, the units are comprised by a single device in such a case. The analyzing unit may comprise the antibody in immobilized form on a solid support. Such an analyzing unit is particular useful for liquid samples. The sample to be investigated with the device of the present invention is preferably a tissue sample and, more preferably, a tissue section sample. Thus, in another aspect, the antibody may be comprised in a detection solution which will be applied to tissue samples such as tissue section by the analyzing unit. The detection solution can be stored in the analyzing unit or a separate vial, even outside the device. The evaluation unit, preferably a computer or data processing device, comprises implemented rules, i.e. an algorithm, for evaluating the binding determined by the analyzing unit whereby the binding is evaluated into significant or non-significant binding based on the signal type, strength and, in the case of tissue samples, position of the signal with respect to the tissue. For samples which are evaluated to show non-significant binding the diagnosis "no cancer" will be established. If significant binding is obtained as result of the evaluation, the diagnosis cancer shall be established The invention finally pertains to a kit for diagnosing cancer comprising an antibody of the invention as specified above.

The term "kit" as used herein refers to a collection of the aforementioned antibody and instructions provided in a ready-to-use manner for diagnosing cancer in a sample. The antibody and the instructions are, preferably, provided in a single container. Preferably, the kit also comprises further components which are necessary for carrying out the diagnosis. Such components may be auxiliary agents which are required for the detection of the antibody binding, agents for pre-treating the sample to be analyzed or calibration standards.

All references cited in this specification are herewith incorporated by reference with respect to their entire disclosure content and the disclosure content specifically mentioned in this specification.

EXAMPLES

The following Examples shall merely illustrate the invention. They shall not be construed, whatsoever, to limit the scope of the invention.

Example 1

Generation of an Antibody That Targets Specifically the BRAF V600E Mutant Polypeptide The synthetic peptide GLATEKSRWSG (SEQ ID NO: 1)matching the BRAF amino acid sequence from position 596 to 606 and harboring the V->E exchange was commercially generated. The Husar software package (DKFZ, Heidelberg, Germany) was used to select the appropriate sequence region. The peptide was conjugated with KLH (keyhole limpet hemocyanine) to form the immunogenic peptide. Six week old female C57 black sex mice (Charles River, Sulzfeld, Germany) were used. Always a 100 µL volume was injected in the hind limps of mice according to the following schedule:

Day 1: 20 µg of the immunogenic peptide dissolved in PBS elucidated 1:1 with complete Freund's Adjuvans was injected into the mice.

Day 5: 20 µg of the immunogenic peptide dissolved in PBS elucidated 1:1 with incomplete Freund's Adjuvans was injected into the mice.

Day 11: 20 µg of the immunogenic peptide dissolved in PBS.

Day 18: 20 µg of the immunogenic peptide dissolved in PBS was injected into the mice.

At day 19 extraction of blood from mice, separation of serum, western blot test against tumor proteins harboring either the BRAF V600E or BRAF wild type protein was carried out. At day 46 20 µg of the immunogenic peptide dissolved in PBS was injected into the mice. At day 47 extraction of blood from mice, separation of serum, western blot test against tumor proteins harboring either the BRAF V600E or BRAF wild type protein was carried out. At day 48 the mouse was sacrificed. Popliteal lymph nodes were removed, cells separated and fused with tumor cells of the line SP2/0 to generate hybridoma cells. Finally, the hybridoma cells were grown, single cells were picked and separated in order to generate pure clones. Supernatants from clones were analyzed by western blot to detect the clones that produce BRAF V600E specific antibodies.

Analysis by Western blotting employing protein extracts from cell lines expressing mutant (V600E) and wild type (wt) BRAF demonstrates binding of the hybridoma clones 53, 62,449 and 263 to BRAF V600E. Thus, these antibodies are highly useful for detecting the BRAF V600E mutation by Western blotting. Clone 263 was deposited under accession number DSM ACC 3091 with the "DSMZ—Deutsche Sammlung von Mikroorganismen and Zellkulturen GmbH", 38124 Braunschweig, GERMANY on Sep. 8, 2010 according to the Budapest Treaty by "Deutsches Krebsforschungszentrum", Heidelberg, GERMANY.

Example 2

The Antibody of Clone 263 Targets Specifically Tumor Cells Expressing the BRAF V600E Mutant Polypeptide in Tissue Sections Formalin fixed and paraffin embedded sections were cut to 4 µm with a Microm HM 355 S™ microtome (Thermo Fisher Scientific, Waltham, Mass., USA) with an electrical cooled object clamp (Cool-Cut™; Thermo Fisher Scientific). Thereafter, the sections were dried at 80° C. for 15 min and stained with anti-BRAF V600E antibody (clone 263) on a Ventana BenchMark XT® immunostainer (Ventana Medical Systems, Tucson, Ariz., USA). The Ventana staining procedure included pretreatment with cell conditioner 1 (pH 8) for 60 min, followed by incubation with undiluted BRAF V600E hybridoma supernatant at 37° C. for 32 min. Antibody incubation was followed by Ventana standard signal amplification including the Ventana amplifier kit, UltraWash, counterstaining with one drop of hematoxylin for 4 min and one drop of bluing reagent for 4 min. For chromogenic detection, ultraView™Universal Red v3 Detection Kit (Ventana Medical Systems) was used. Subsequently, slides were removed from the immunostainer, washed in water with a drop of dishwashing detergent and mounted. No chromogen was detected when primary antibody BRAF V600E (clone 263) was omitted. Immunoreaction was scored positive when tumor cells showed a strong cytoplasmic staining for BRAF V600E. A weak diffuse staining and staining of macrophages were not scored positive.

Figure 1:
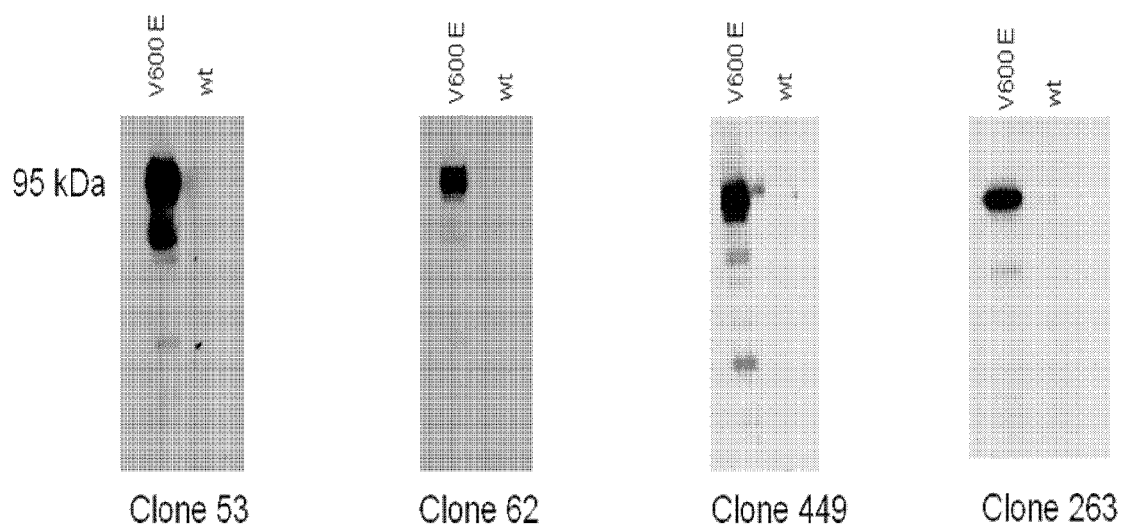
Figure 2:
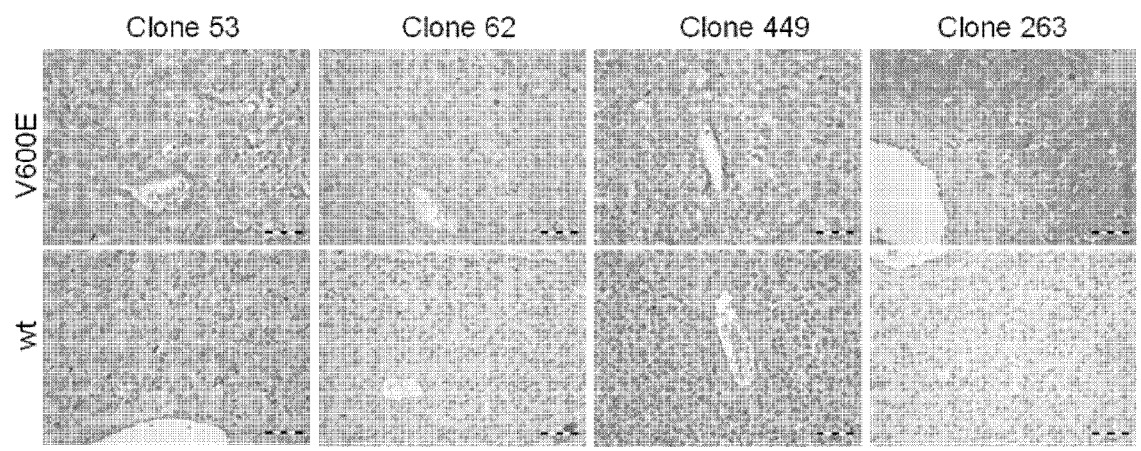
FIG. 2 shows immunostainings of tissue sections from V600E BRAF positive tumors (formalin fixed and paraffin embedded melanomas) and controls from melanomas having wildtype BRAF as confirmed by genomic sequence analysis. Immunostaining was merely observed among all tested clones with the antibodies produced by the hybridoma clone 263.
Figure 3:
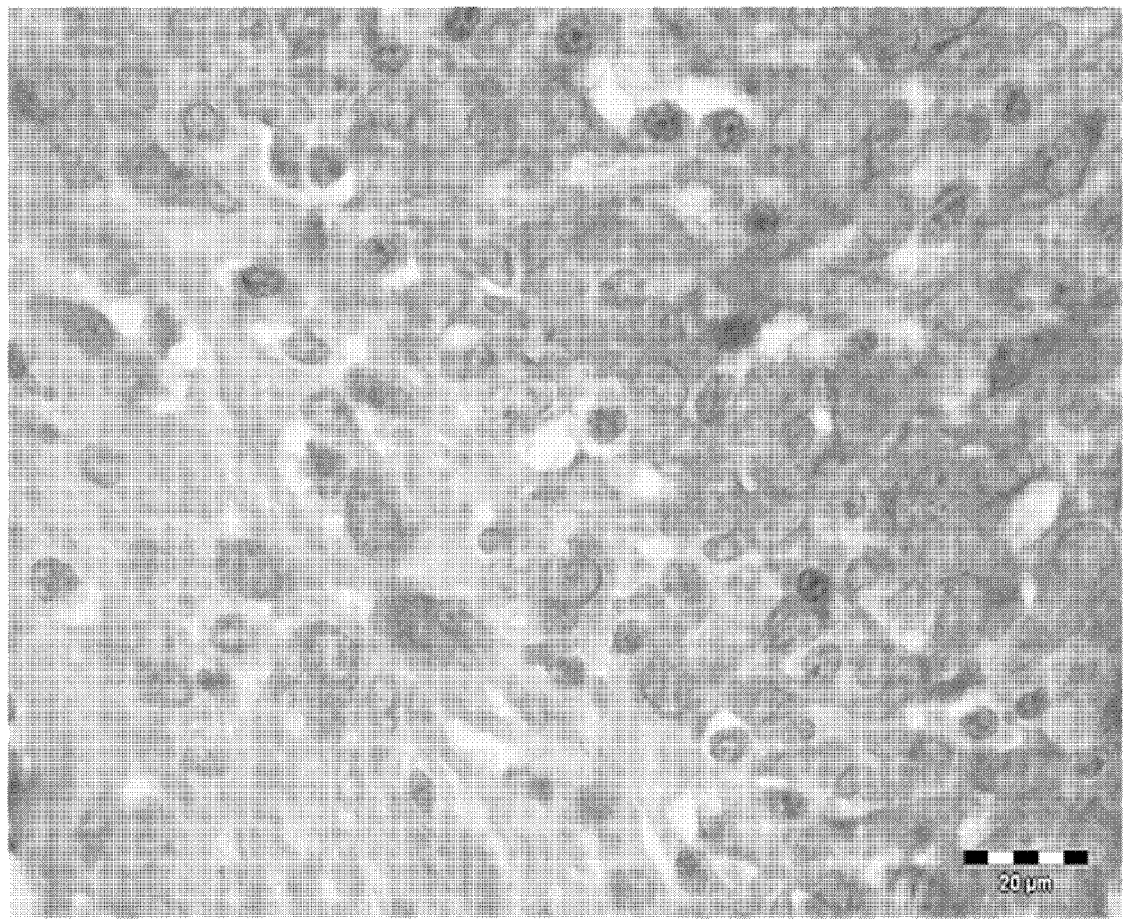
FIG. 3 shows a magnification of an area from the tissue section shown in FIG. 2 which has been immunostained with the antibody of hybridoma clone 263. The figure shows that the antibody stains the cytoplasm of the tumor cells and, thus, the site of subcellular location of the V600E BRAF polypeptide.

Analysis of BRAF V600E mutations by immunohistochemistry on formalin fixed and paraffin embedded tissue sections from tumors with predetermined sequence status demonstrates exclusive binding of hybridoma clone 263 (see FIG. 2) to BRAF V600E mutant melanoma but not to melanoma wild type for BRAF. Importantly, the clones 53, 62 and 449 shown in FIG. 1 also to bind to BRAF V600E by Western blotting do not recognize this mutation on formalin fixed and paraffin embedded tissue sections. Specific binding, however, was observed only for the specific mouse clone 263 (see FIG. 2 and at higher magnification in FIG. 3).

Clone 263 was deposited under accession number DSM ACC 3091 with the "DSMZ—Deutsche Sammlung von Mikroorganismen and Zellkulturen GmbH", 38124 Braunschweig, GERMANY on Sep. 8, 2010 according to the Budapest Treaty by "Deutsches Krebsforschungszentrum", Heidelberg, GERMANY.

Example 3

The Antibody of Clone 263 Targets Specifically Identifies Hairy Cell Leukemia Expressing the BRAF V600E Mutant Polypeptide All human materials were obtained from the Tissue Bank of the National Center for Tumor Diseases (NCT) and the Department of General Pathology, Institute for Pathology, Heidelberg. Tissue microarrays (TMA) constructed from paraffin embedded tissues together carrying 208 cases of mature B-cell neoplasms including plasmacytoma (n=26), follicular lymphoma (n=34), diffuse large B-cell lymphoma (n=41), primary mediastinal B-cell lymphoma (n=25), mantle cell lymphoma (n=17), extranodal marginal zone lymphoma (n=16), hairy-cell leukemia (n=3) and Hodgkin's lymphoma (n=46) were analyzed. For further examination, additional full sections from bone marrow (n=34) or spleen (n=1) with hairy cell leukemia (total n=35) and bone marrow with splenic marginal zone lymphoma (SMZL) (n=4) were assessed.

Immunohistochemistry was carried out as follows: The sections from TMA and bone marrow or spleen were cut to 4 microns, dried at 80° C. for 15 minutes and exposed to BRAF$_{V600E}$ specific mouse monoclonal antibody (clone VE1) on an automated immunostainer (Ventana BenchMark XT, Ventana Medical Systems, Tucson, Ariz., USA) using standard reagents provided by Ventana. Pretreatment with cell conditioner 1 was followed by incubation with VE1 hybridoma supernatant at 37° C. for 32 min and consecutive signal enhancement by the amplifier kit, ultra-Wash, chromogenic detection with ultraView Universal DAB detection kit and counterstaining with hematoxilin and bluing reagent for 4 min each. The immunostained slides were evaluated by three pathologists (DC, AvD, MA) without knowledge of the mutation status.

BRAF V600E was also detected by direct DNA sequencing. DNA was extracted from formalin-fixed paraffin-embedded (FFPE) of patients with HCL and SMZL (n=39). Primer sequences and direct sequencing procedure have been described previously (Schindler 2011, Acta Neuropathol 121: 397-405).

The screening of the 208 adult mature B-cell lymphomas for activating BRAF-V600E mutations with a BRAF$_{V600E}$-specific antibody resulted in the identification of two positive samples among three cases of HCL. All other lymphoma cases were negative. Analysis of additional 34 HCL bone marrow biopsies and one spleen biopsy not included on the initial tissue microarray analysis demonstrated a strong cytoplasmic expression of mutated BRAF$_{V600E}$ protein in 31 of 35 cases (87%). Direct sequencing of genomic DNA confirmed the presence of the BRAF-V600E exchange in 24 of 31 (77%) immunohistochemically positive HCL cases. In seven BRAF-V600E expressing bone marrow biopsies BRAF mutation was not detectable by direct sequencing. In two of these 7 cases tumor cell content was below 15%. A representative case is shown in FIG. 4. However, in the remaining 5 cases more than 50% of the cells were HCL. Problems related to processing DNA from FFPE material might be responsible for the false negative direct sequencing results. Importantly, no BRAF-V600E mutations were detected in the 4 immunonegative cases. In addition, no other BRAF codon 600 mutations were identified. These data demonstrate that activating BRAF-V600E mutation are a very frequent event in HCL. This strongly suggests that mutated BRAF is a key molecular mechanism leading to constitutive ERK activation and may represent an essential molecular event in the oncogenic transformation of HCL. Furthermore, the findings indicate that immunohistochemistry with a BRAF$_{V600E}$ mutation-specific antibody is likely more sensitive than direct DNA sequencing for detection of BRAF-V600E mutation in low tumor cell burden lymphomas. Therefore BRAF$_{V600E}$ specific antibody may represent an important new marker to confirm HCL diagnosis and to monitor minimal residual disease. Moreover, the present results imply that HCL could respond to a new generation of molecular compounds that specifically inhibit BRAFv600E activity. Taken together these findings indicate that BRAF-V600E mutation is a crucial molecular event in the pathogenesis of HCL and is readily detected by immunohistochemistry with VE1.

The invention claimed is:
1. The antibody produced by the cell line deposited under accession number DSM ACC 3091.
2. A device for diagnosing cancer comprising
   a) an analyzing unit comprising the antibody of claim 1, wherein said analyzing unit allows for the determination of specific binding of the antibody to the epitope characterized by SEQ ID NO: 1 in the BRAF polypeptide in a sample applied to the analyzing unit; and
   b) an evaluation unit which comprises implemented rules for evaluating the binding determined by the analyzing unit and for establishing a diagnosis.
3. The device of claim 2, wherein said sample is a tissue sample.
4. The device of claim 3, wherein said tissue sample is a tissue section sample.
5. A kit for diagnosing cancer comprising the antibody of claim 1.
6. A method for diagnosing cancer in a sample of a subject suspected to suffer from cancer comprising:
   a) contacting the sample with the antibody of claim 1 under conditions which allow for binding of said antibody to the epitope; and
   b) determining binding of the antibody to the epitope, whereby cancer is diagnosed.
7. The method of claim 6, wherein said diagnosing cancer comprises determining the presence or absence of cancer cells.
8. The method of claim 7, wherein said cancer cells are within a tissue sample.
9. The method of claim 8, wherein said tissue sample is a tissue section sample.
10. The method of claim 6, wherein said method further comprises the step of recommending, or not, an anti-cancer therapy based on the diagnosis obtained in step b).

SEQUENCE LISTING

```
<160> NUMBER OF SEQ ID NOS: 3

<210> SEQ ID NO 1
<211> LENGTH: 11
<212> TYPE: PRT
<213> ORGANISM: Homos sapiens

<400> SEQUENCE: 1

Gly Leu Ala Thr Glu Lys Ser Arg Trp Ser Gly
1               5                   10

<210> SEQ ID NO 2
<211> LENGTH: 9
<212> TYPE: DNA
<213> ORGANISM: Homo sapiens

<400> SEQUENCE: 2 acagtgaaa                                                              9

<210> SEQ ID NO 3
<211> LENGTH: 9
<212> TYPE: DNA
<213> ORGANISM: Homo sapiens

<400> SEQUENCE: 3 acagagaaa                                                              9
```

11. The method of claim 10, wherein said anti-cancer therapy is selected from the group consisting of: anti-BRAF antisense RNA, siRNA or micro RNA drugs, anti-BRAF antibodies, sorafenib, RAF-265, PLX-4032, cetuximab and GDC-0879.

\* \* \* \* \*